(12) United States Patent
Bouquet

(10) Patent No.: US 8,460,187 B2
(45) Date of Patent: Jun. 11, 2013

(54) VAGINAL SPECULUM

(76) Inventor: Jean Bouquet, Parker, CO (US)

( * ) Notice: Subject to any disclaimer, the term of this patent is extended or adjusted under 35 U.S.C. 154(b) by 102 days.

(21) Appl. No.: 13/224,421

(22) Filed: Sep. 2, 2011

(65) Prior Publication Data

US 2013/0060095 A1    Mar. 7, 2013

(51) Int. Cl.
*A61B 1/32* (2006.01)
(52) U.S. Cl.
USPC .......................................... 600/222; 600/223
(58) Field of Classification Search
USPC .................. 600/203, 190, 186, 184, 196, 201,
600/210, 214, 215, 219–225, 235, 208, 207,
600/193, 198; 606/192, 193
See application file for complete search history.

(56) References Cited

U.S. PATENT DOCUMENTS

| | | | |
|---|---|---|---|
| 5,174,278 A | 12/1992 | Babkow | |
| 5,505,690 A | 4/1996 | Patton et al. | |
| 5,716,329 A * | 2/1998 | Dieter | 600/210 |
| 5,795,289 A | 8/1998 | Wyttenbach | |
| 6,036,638 A | 3/2000 | Nwawka | |
| 6,126,594 A * | 10/2000 | Bayer | 600/184 |
| 6,280,379 B1 | 8/2001 | Resnick | |
| 6,364,832 B1 | 4/2002 | Propp | |
| 6,432,048 B1 | 8/2002 | Francois | |
| 7,060,029 B1 | 6/2006 | Hajianpour | |
| 7,736,299 B2 * | 6/2010 | Klenk et al. | 600/37 |
| 2005/0021080 A1 | 1/2005 | Feuer et al. | |
| 2005/0192482 A1 | 9/2005 | Carpenter et al. | |
| 2006/0079924 A1 | 4/2006 | Sanders et al. | |

* cited by examiner

*Primary Examiner* — Pedro Philogene
(74) *Attorney, Agent, or Firm* — Marsh Fischmann & Breyfogle LLP; Kent A. Fischmann

(57) ABSTRACT

A vaginal speculum, conical in shape made out of clear plastic resin or metal that when closed can easily and gently be inserted into the introitus (vaginal opening). In certain embodiments, an obturator is used to introduce and/or expand the speculum. Various mechanisms are disclosed for dilating the speculum, after it has been inserted, so as to allow inspection of the patient's cervix. Such dilation can be effected relative to multiple axes, or even in substantially continuous, radial fashion about the periphery of the speculum, for improved visualization. In addition, this speculum has a handle that is oriented such that a vaginal exam can be performed on a standard exam table. The handle also includes a receptacle that receives a standard pen light. A light pipe directs light from the pen light to illuminate the cervix.

14 Claims, 11 Drawing Sheets

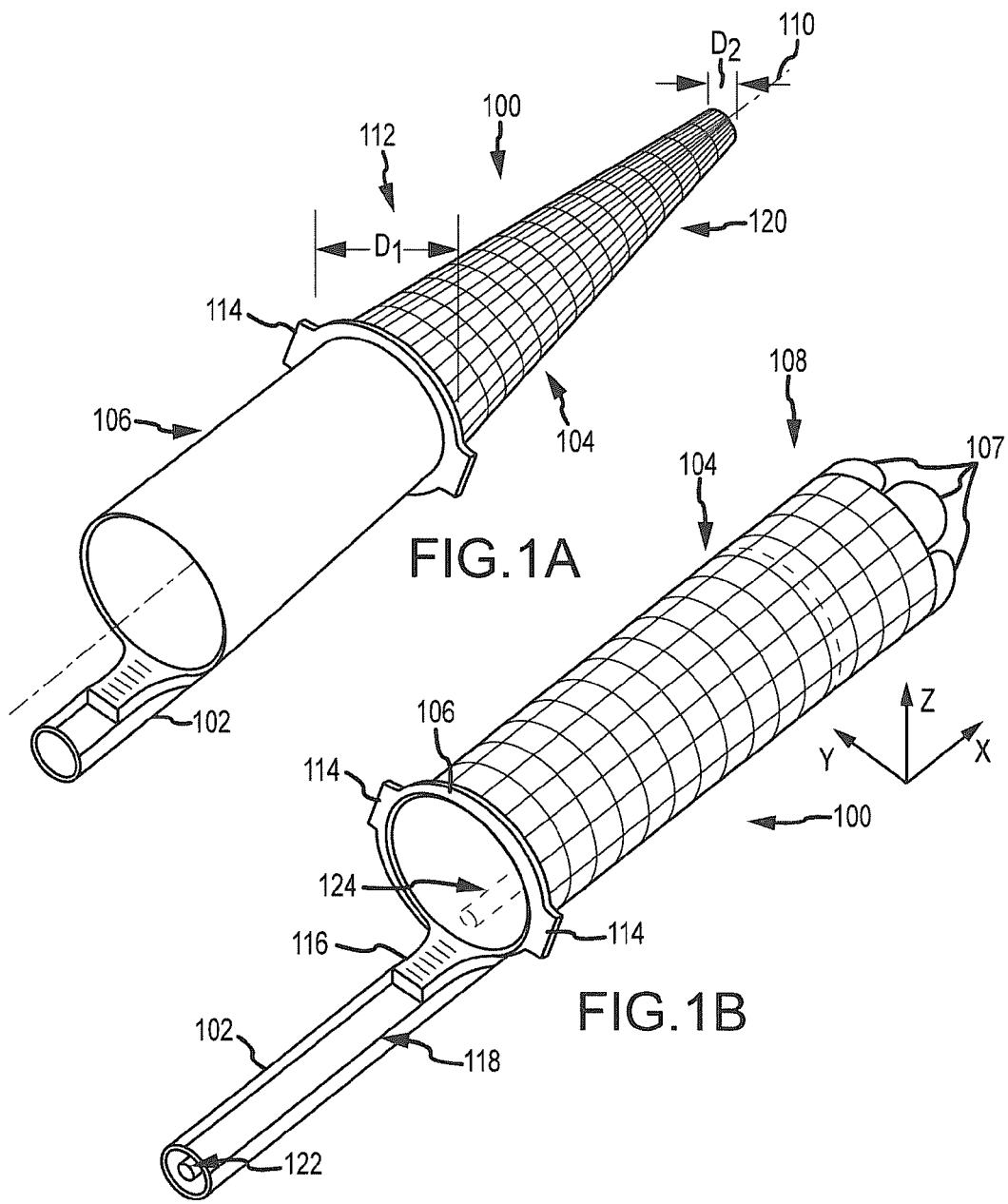

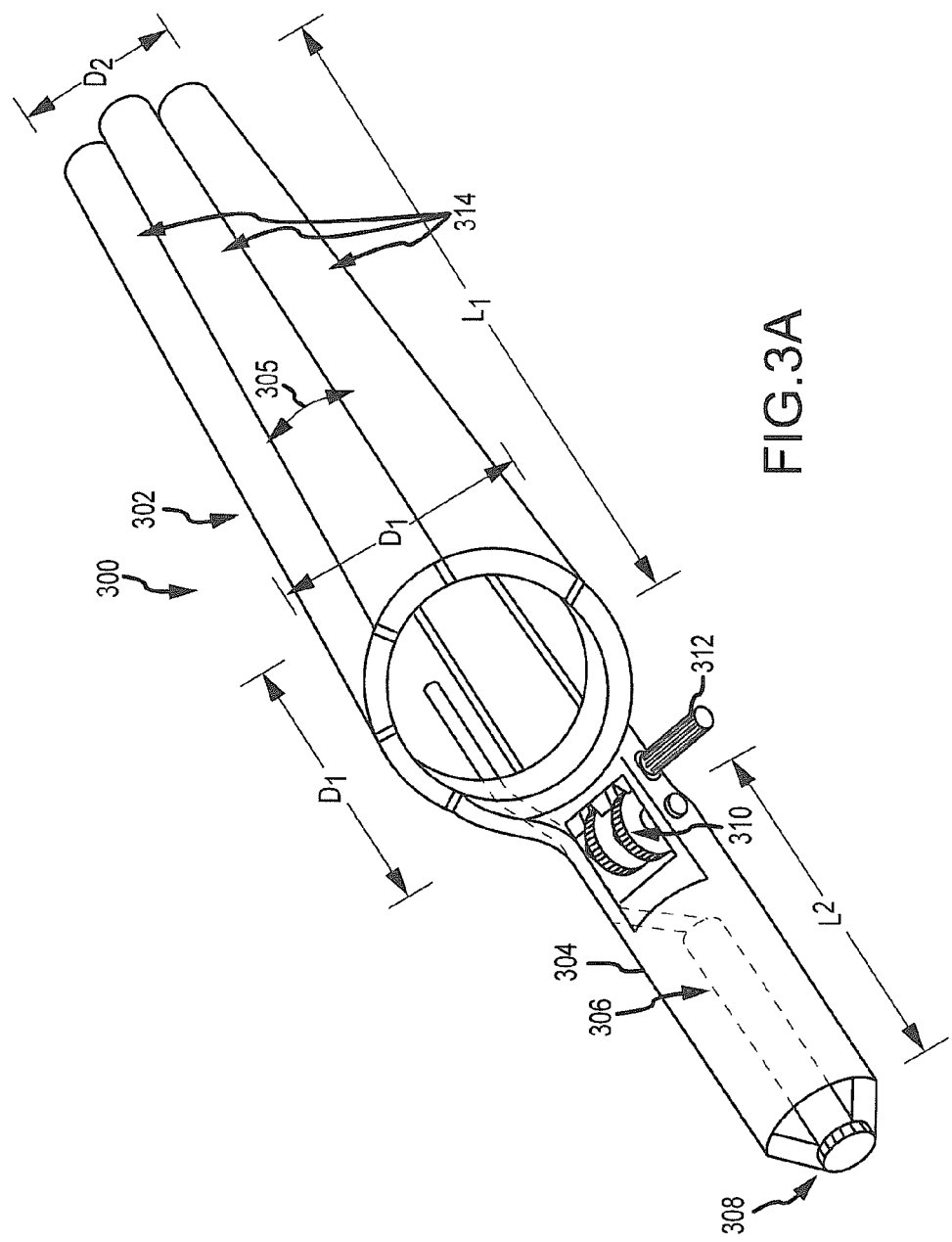

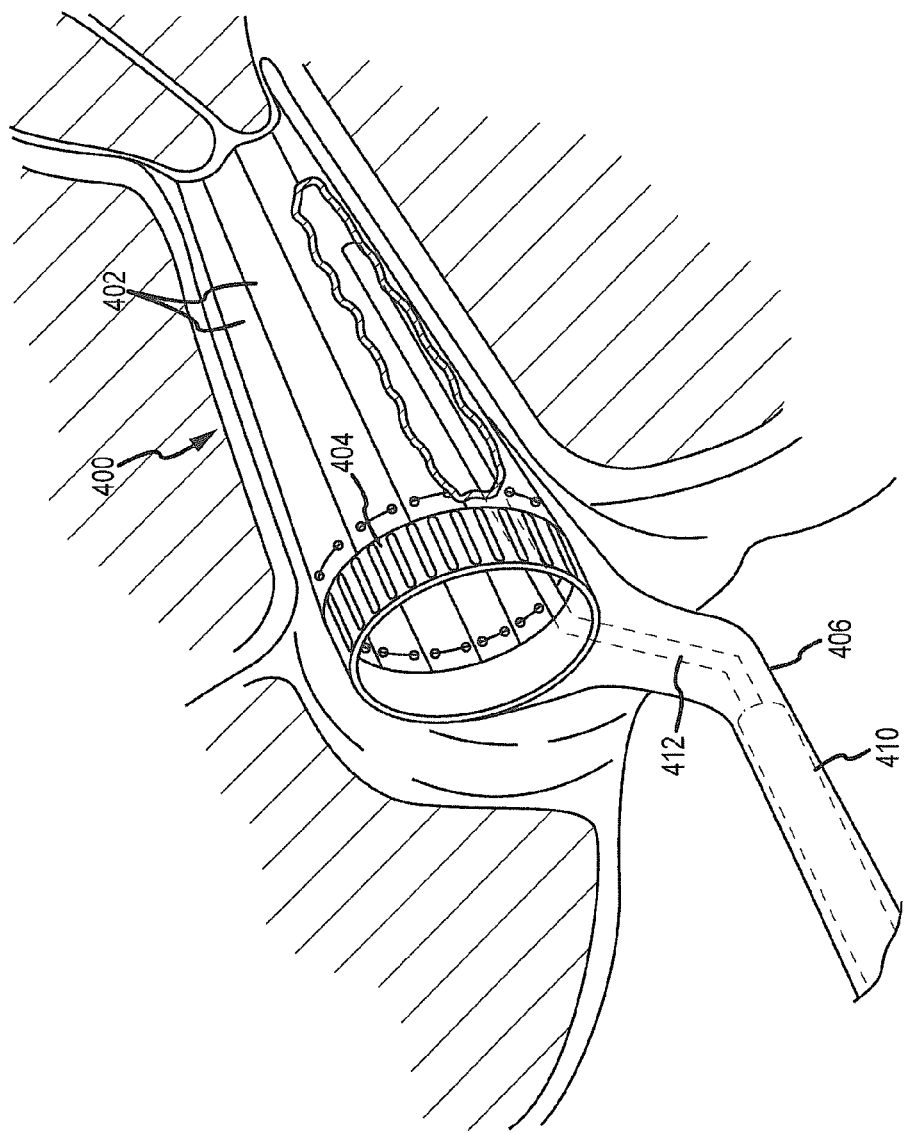

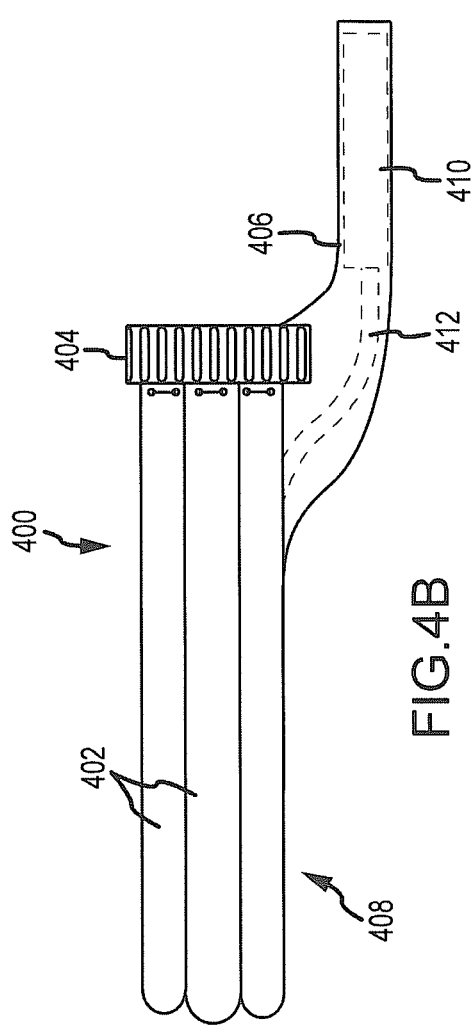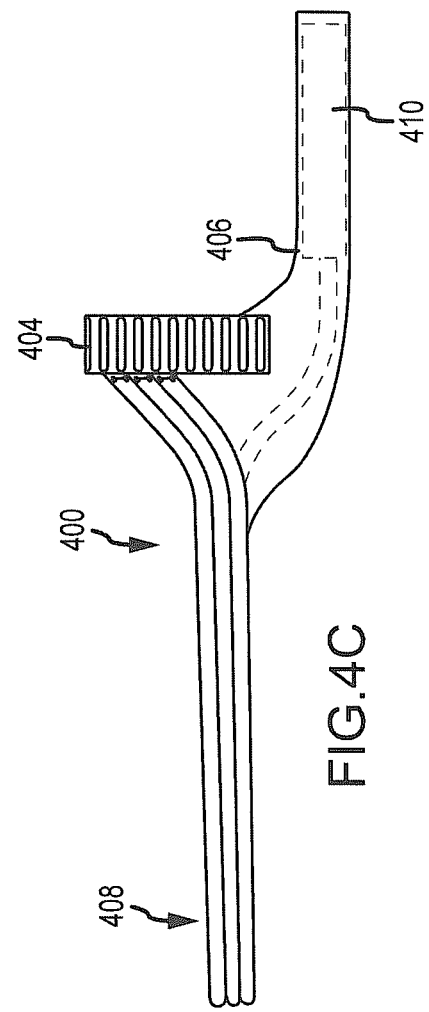
FIG.4B
FIG.4C

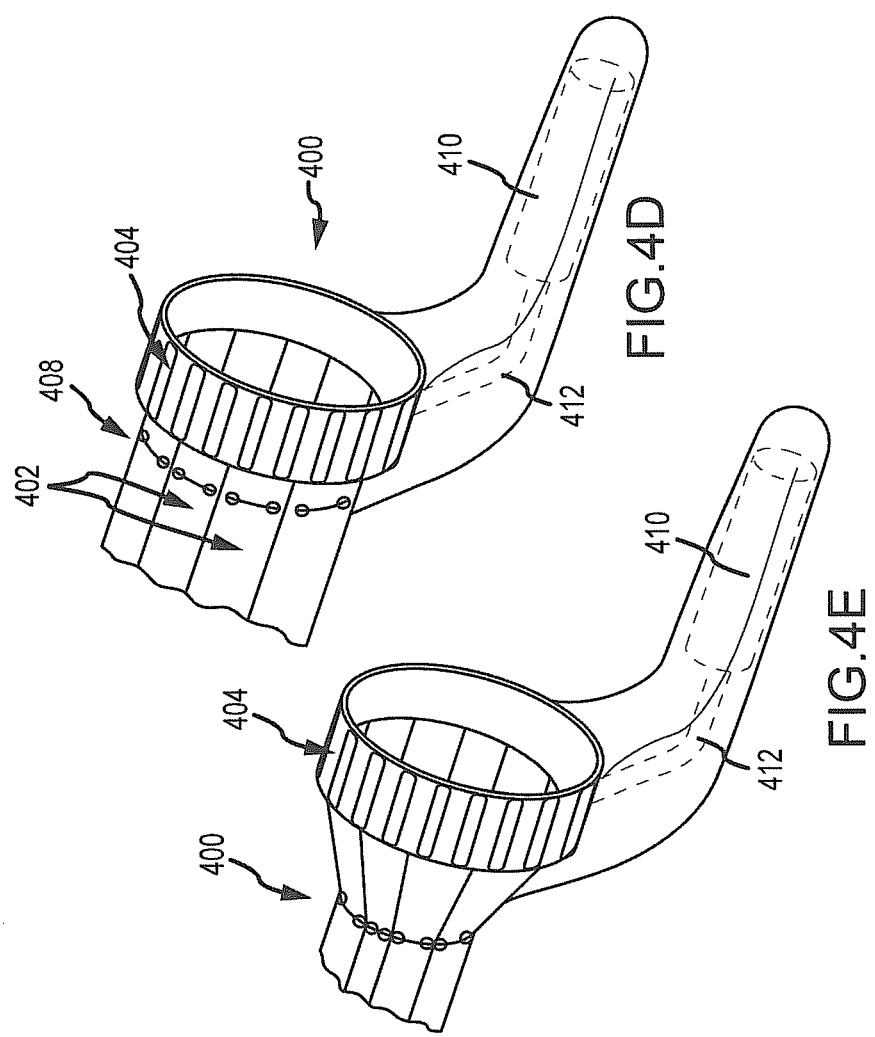

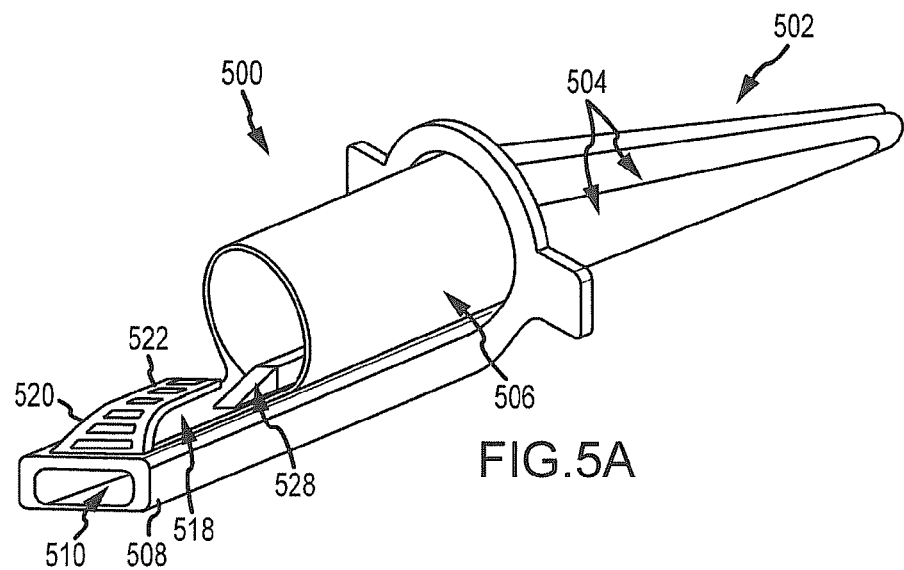
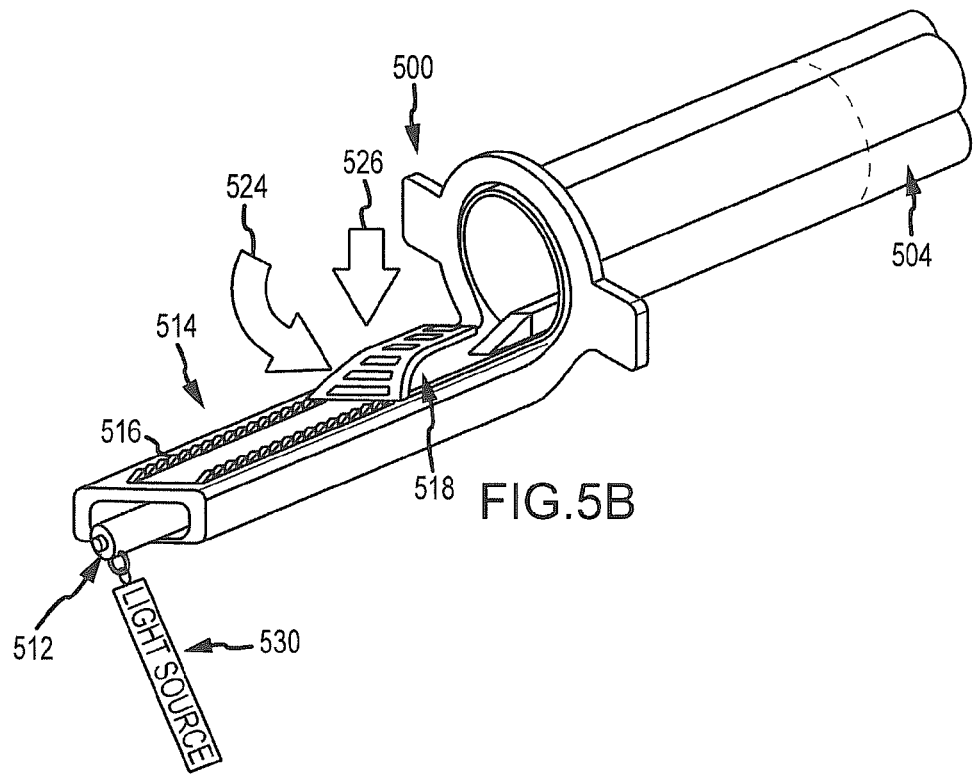

VAGINAL SPECULUM

FIELD OF THE INVENTION

The present invention relates to vaginal specula and, in particular, to a radially expanding speculum that improves visualization of the cervix and thereby enhances cervical analysis and procedures.

BACKGROUND

Vaginal specula are used to dilate the vagina and visualize the uterine cervix to screen and treat for cancerous and benign lesions of the cervix. Generally, existing vaginal specula are two-bladed including a stationary blade (relative to the speculum handle) and a pivoting blade. Some designs allow the pivot point to move linearly away from the stationary blade. Nonetheless, the blades are substantially limited to moving apart and back together in relation to one axis.

There are several drawbacks to existing speculum designs. The most important of these is the potential failure to fully visualize the cervix which could lead to failure to diagnose cervical cancer-a life threatening condition. In some women, with the two-bladed speculum, the vaginal walls collapse between the two-blades and obscure the view of the cervix. The current two-blade design has relatively large blades that are difficult to introduce into the vagina of an apprehensive patient. In addition the current speculum also does not take into account the variation in patient anatomy. The uterine cervix typically sits at a 90° angle to the vagina. The two-bladed speculum, as designed, opens asymmetrically. This may cause excessive dilatation in certain parts of the vagina thus causing discomfort to the patient.

Moreover, when closing and removing the two-bladed speculum, there are two "pinch points" along the length of the blade members, which can cause patient discomfort upon closing of the blades in preparation for withdrawal. In addition, the current handles on vaginal speculums are generally oriented at 90 degrees relative to the blades necessitating a specialized gynecologic table with stirrups. Certain existing specula also require a halogen light source that is costly and requires AC/DC current. Lastly, the current speculum on the market when opened creates a very disconcerting clicking sound.

SUMMARY

The present invention provides a new and unique design for a vaginal speculum that reduces or eliminates these existing drawbacks. The ideal speculum, in accordance with the present invention, would be comfortable and non-threatening for the patient, consistently accurate at visualizing the cervix, universal for all body types and anatomy, simple and easy to use for the clinician, and cost effective to manufacture and use on an ongoing basis.

In accordance with one aspect of the present invention, a vaginal speculum is provided that expands in more than one dimension. As noted above, a common type of speculum on the market today expands substantially only in relation to a single dimension. That is, the speculum has two-blades, one of which pivots about an axis so that the associated blade moves on an arcuate path away from or towards the stationary blade. Although the moveable blade and its pivot point may also be moved linearly towards or away from the stationary blade, expansion of the speculum is still substantially limited to a single axis transverse to the longitudinal axis of the blades. This has a number of disadvantages, as described above, including that the vaginal walls of some patients can collapse between the blades impairing visualization of the procedure site.

The inventive speculum in accordance with the present aspect of the invention includes a handle, a dilation assembly for separating and retaining the vaginal walls of a patient and a dilation actuator. The dilation assembly has a proximal end portion near the handle and a distal end portion remote from the handle and is movable between a contracted configuration, wherein the distal end portion has a reduced circumference, and expanded configuration wherein the distal end portion is expanded for improved visualization of the cervix. The dilation actuator is operative to expand the distal end portion of the dilation assembly in relation to at least a first axis and a second axis transverse to the first axis.

Unlike conventional specula that have a stationary blade (fixed in relation to the handle) and a moveable blade, the inventive speculum may include multiple (two or more) moveable blades. Moreover, the inventive speculum preferably has at least three blades. In one embodiment, the speculum has three or more blades, each of which moves outward from a central axis of the dilation assembly. In some embodiments the blades move radially outward whereas, in other embodiments, the blades expand radially outwardly while concomitantly traveling circumferentially in relation to the central axis. Such movement may be actuated by an obturator which is inserted into a hollow interior of the dilation assembly, and withdrawn therefrom, so as to move between the expanded and contracted configurations. The obturator may be moved into and out of the dilation assembly in linear fashion or by operation of a screw mechanism. The speculum may also include a light source receptacle assembly for receiving a light source so that light can be transmitted through the dilation assembly to a procedure site.

In accordance with another aspect of the present invention, a method for using a vaginal speculum is provided. The method includes the steps of: introducing a dilation assembly of a speculum into the introitus of a patient; operating a dilation actuator to expand the dilation assembly with respect to a first axis and with respect to second axis transverse to the first axis; upon concluding a medical procedure, operating the dilation actuator to contract the dilation assembly to a contracted configuration; and withdrawing the dilation assembly from the introitus of the patient. The step of expanding the dilation assembly may involve, for example, advancing an obturator into a hollow interior of the dilation assembly from a proximate end of the dilation assembly so as to force the dilation assembly into the expanded configuration. The process may further involve operating a light source mounted in a handle of the speculum to transmit light through the dilation assembly so as to illuminate the procedure site.

BRIEF DESCRIPTION OF THE DRAWINGS

For a more complete understanding of the present invention, and further advantages thereof, reference is now made to the following detailed description taken in conjunction with the drawings in which:

FIGS. 1A and 1B show perspective views of a vaginal speculum, constructed in accordance with the present invention, in a contracted (closed) and an expanded (open) configuration, respectively;

FIGS. 3A and 3B are perspective views of a vaginal speculum, in accordance with an alternate embodiment of the present invention, in expanded and contracted configurations, respectively;

FIG. 4A shows a speculum, in accordance with a still further embodiment of the present invention, positioned for inspection of a patient's cervix;

FIGS. 4B-4C are side views showing the speculum of FIG. 4A in the open and closed configurations respectively;

FIGS. 4D-4E show perspective views of a portion of the speculum of FIG. 4A in the open and closed configurations, respectively;

FIGS. 5A-5B, are perspective views of a speculum, in accordance with another embodiment of the present invention, in closed and open configurations, respectively;

DETAILED DESCRIPTION

Figure 2A:
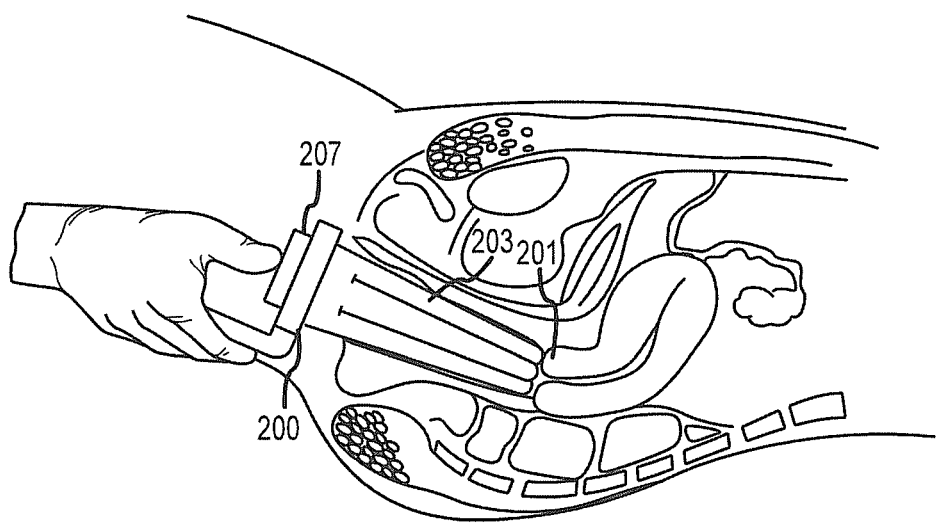
FIGS. 2A and 2B illustrate a vaginal speculum in accordance with the present invention in contracted and expanded configurations, respectively, where the speculum in shown inserted into the introitus of a patient and certain physiology of the patient is depicted for purposes of illustration.

In the following description, the invention is set forth with respect certain specific embodiments of vaginal specula. While these embodiments illustrate the principles of the present invention, it is anticipated that further embodiments of the invention are possible and will be apparent to those skilled in the art upon consideration of the present disclosure. Accordingly, the invention is not limited to the embodiments as set forth herein.

FIGS. 1A and B illustrate perspective views of a speculum 100 in accordance with the present invention. Specifically, FIG. 1A illustrates the speculum 100 in contracted or closed configuration and FIG. 1B illustrates the speculum 100 in an expanded or open configuration. The speculum 100 includes a handle 102 for gripping by a physician or other user, a dilation assembly 104 for dilating and retaining the vaginal walls of the patient so as to facilitate visual inspection of the uterine walls and cervix as well as associated medical procedures, and an obturator 106 for use in introducing the dilation assembly 104 into the patient and for forcing the dilation assembly 104 to the expanded configuration as shown in FIG. 1B. Withdrawing the obturator 106 from the dilation assembly 104 allows the dilation assembly 104 to return to the contracted configuration as shown in FIG. 1A.

The illustrated dilation assembly 104 includes a number of blades 107. As will described in more detail below, at the distal end 108 of the dilation assembly 104, remote from the handle 102, the blades 107 can spread apart from one another so as to define the expanded configuration and can come back together in order to define the contracted configuration. The dilation assembly 104 preferably includes at least three blades 107 to allow expansion with respect to at least two axes or two dimensions, e.g., the Y and Z dimensions as shown in FIGS. 1A and 1B where the X, Y and Z axes are mutually orthogonal and the X axis is aligned with the longitudinal axis 110 of the dilation assembly 104. The illustrated dilation assembly 104 includes four blades 107 each of which extends about approximately one quarter or 90° of the periphery of the dilation assembly 104 at the distal end 108 in the contracted configuration. The blades 107 may alternatively overlap or remain somewhat separated (e.g., to avoid pinching) in the contracted configuration.

The dilation assembly 104 has a generally hollow, truncated conical or bullet-shaped configuration. In the contracted configuration as shown in FIG. 1A, the dilation assembly 104 has a diameter, $D_1$, at the proximal end 112, thereof, adjacent the handle 102 of about two inches and a diameter, $D_2$, at the distal end thereof about 0.75 inches. In the expanded configuration as shown in FIG. 1B, the diameter $D_2$ is, for example, about 1.5 inches. The illustrated dilation assembly 104 further includes finger grips 114 that may be gripped by the physician or other user to facilitate insertion of the obturator 106 as will be described in more detail below. The dilation assembly 104 as well as the handle 102 and/or obturator 106 may be formed from a clear plastic resin, other plastic or metal. In this regard, plastic or resin materials allow for low cost construction as may be desired for single use disposable applications. The speculum 100 may be constructed from metal materials to allow for sterilization and reused if desired. In the illustrated embodiment, the dilation assembly 104 is formed from a clear plastic resin.

For example, the body of the dilation assembly 104 may be constructed by obtaining or molding the plastic resin in generally cylinderal or conical shape. The plastic resin can then be cut or slit from the distal end toward the proximate end 112 to define the blades 107. Alternatively, the blades 107 may be formed by appropriate molding. In any event, the blades 107 in the illustrated embodiment do not extend the full length of the dilation assembly 104. Rather, the blades 107 come together at a location near the proximal end 112 to form a continuous cylinderal side wall. In this manner, the blades 107 flex outwardly to the expanded configuration when the obturator of 106 is advanced into the hollow interior of dilation assembly 104 from the proximal end 112. When the obturator is withdrawn from the hollow interior of the dilation assembly 104, the blades 107 collapse to the contracted configuration, e.g., due to material memory of the clear plastic resin material or forces exerted on the exterior of the dilation assembly 104 by the vaginal walls of the patient or by the user. Where metal materials are utilized, the dilation assembly 104 can move between the expanded and the contracted configurations by flexing of the metal materials or by hinge mechanisms.

As noted above, the obturator 106 may be formed from plastic, metal or other materials. In the illustrated embodiment, the obturator is formed from a clear plastic resin material. The obturator 106 may have a generally cylindrical or conical configuration and is dimensioned to be received within the hollow interior of the dilation assembly 104 at the proximal end 112 thereof. That is, the outside diameter of the obturator 106 (at least the proximal end thereof) is slightly smaller than the inside diameter of the dilation assembly 104 at the proximal end 112. For example, the outside diameter of the obturator 106 at its proximal end thereof may be between about 1.5 and 2 inches.

The illustrated obturator 106 has a thumb grip 116 extending from the rear surface thereof. The thumb grip 116 can be gripped by the user to advance the obturator 106 into dilation assembly 104 and to withdraw the obturator 106 from the dilation assembly 104. In the illustrated embodiment, the obturator 106 includes a rib (not shown) extending from the bottom of the obturator. This rib and/or the bottom of thump grip 116 runs in a longitudinal obturator track 118 formed in an outer surface of the handle 102 so as to guide the longitudinal movement of the obturator 106. The thumb grip 116 may be ergonomically shaped and textured so as to facilitate operation by a physician or other user. In the case of a conical obturator 106 can be inserted, distal end first, into the dilation assembly 104 to facilitate introduction of the dilation assembly 104 into the introitus. The obturator can then be flipped and reinserted into the dilation assembly 104 proximal (fat) end first to expand the dilation assembly 104 to the extent desired. In the case of a cylindrical obturator 106, the obturator 106 would be advanced into the dilation assembly 104 only after the dilation assembly 104 is positioned within the introitus. In such cases, the dilation assembly 104 may be bullet-shaped to better resist blade separation during introduction. In this regard, a cylindrical obturator 106 may facilitate better visualization as it provides a wide aperture across its entire length. The obtuator may be advanced linearly (and may thereafter maintain its position by friction or a ratchet mechanism) or may be threaded so as to advance into the dilation assembly 104 via a rotary, screw-like motion.

The illustrated speculum 100 also includes a silicone sleeve 120 to protect against penetration of the vaginal walls between the blades and potential pinching. As can be seen in FIG. 1B, the blades 107 are separated from one another by spaces in the expanded configuration. As the blades 107 collapse to the contracted configuration, the edges of the blades come together creating a risk that of tissue of a patient will be captured there between and pinched. This risk can be reduced by use of the optional silicone sleeve 120. The silicone sleeve 120 can be placed over the dilation assembly 104 at one end thereof and unrolled like a condom to extend around substantially the entire external surface of the dilation assembly 104. In this manner, the silicone sleeve 120 guards against collapsing of the patient's uterine wall tissue into the spaces between the blades 107.

The handle 102 of the illustrated embodiment has a generally cylindrical configuration. If desired, the exterior surface of the handle 102 may be formed for improved ergonomics. The illustrated handle 102 has a hollow interior cylinder receptacle 122 dimensioned to receive a light source. The light source can be activated by the user to transmit light through the handle 102 and through the dilation assembly 104 so as to illuminate a procedure site such as the patient's uterine walls and/or cervix. In the illustrated embodiment a light pipe 124 is formed in a portion of the dilation assembly 104 to guide light to and concrete light on the procedure site. Conventional vaginal specula typically require an expensive custom light source. Though such light sources can be provided in connection with illustrated speculum 100, the illustrated speculum 100 can also be designed to receive an inexpensive pen light within the cylinder receptacle 122. The cylinder receptacle 122 may be formed so that the pen light is turned on, e.g., by depressing a button on the pen light, when the pen light is inserted into the cylinder receptacle 122. Alternatively, the pen light may have an on/off button exposed at a rear end thereof that can be accessed by the user after the pen light is inserted into cylinder receptacle 122.

Figure 2B:
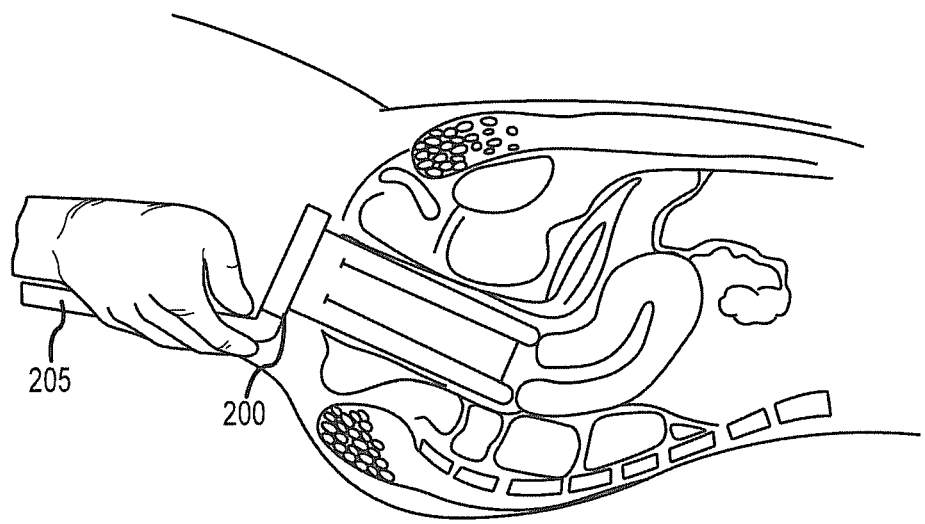

FIGS. 2A and 2B illustrate a speculum 200, generally similar in construction to the speculum 100 of FIGS. 1A and 1B but with a slightly different configuration, in use on a patient. Specifically, in use, the speculum 200 can be introduced into the introitus of the patient in a contracted configuration as shown in FIG. 2A. As shown, the speculum 200 is advanced into the patient until the distal end of the speculum 200 is adjacent to the patient's cervix 201. It will be appreciated that the speculum 200 is dimensioned appropriately in this regard. For example, the dilation assembly 203 may have a length of about 6.5 inches and the handle 205 may have a length of about 3.5 inches for an overall speculum length of about 10 inches. Such dimensions are believed to accommodate a substantial range of physiological variability among patients. Once the speculum 200 has been inserted to the full extent desired, the physician or other user can advance the obturator 207 into the proximal end of the dilation assembly 203 so that the blades of the dilation assembly are radially separated.

It will be appreciated, that, in the case of a four bladed dilation assembly as described in connection with FIGS. 1A and 1B, two of the blades may separate along a front to back axis with respect to the patient and two of the blades may separate along a side to side axis with respect to the patient. This creates an unobstructed view. The blades may be formed to separate along other axes if desired. The user can then insert or otherwise activate a light source at the speculum handle 205 to illuminate the uterine walls and cervix of the patient. The physician or other user can then visually inspect the uterine walls and cervix of the patient by looking through the hollow interior of the obturator 207 and dilation assembly 203 to obtain a clear view of the procedure site. When the inspection or any other desired procedure (e.g., obtaining an analysis sample by introducing an instrument through the hollow interior of the speculum) is complete, the obturator 207 is withdrawn from the dilation assembly 203 allowing the dilation assembly 203 to collapse to the contracted configuration. The speculum 200 can then be withdrawn from the patient's introitus and disposed of and or sterilized as appropriate.

FIGS. 3A-3G illustrates a speculum 300 constructed in accordance with alternative embodiment of the present invention. The speculum 300 generally includes a dilation assembly 302 a handle 304 including a receptacle 306 for holding a light source 308 and a ratchet assembly 310 for use in expanding the dilation assembly 302. The ratchet assembly 310 is operated using a thumb lever 312.

Figure 3B:
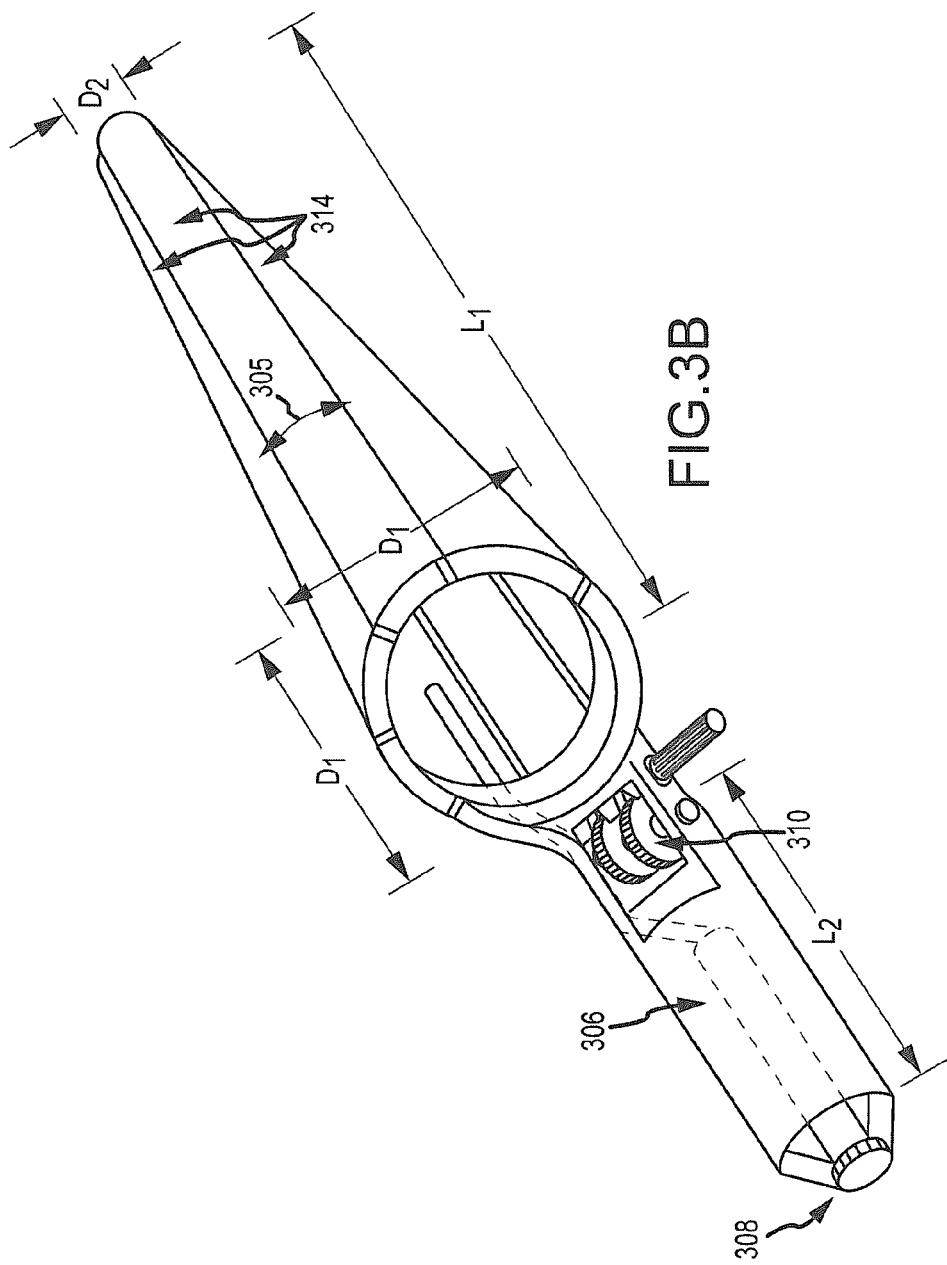
Figure 3C:
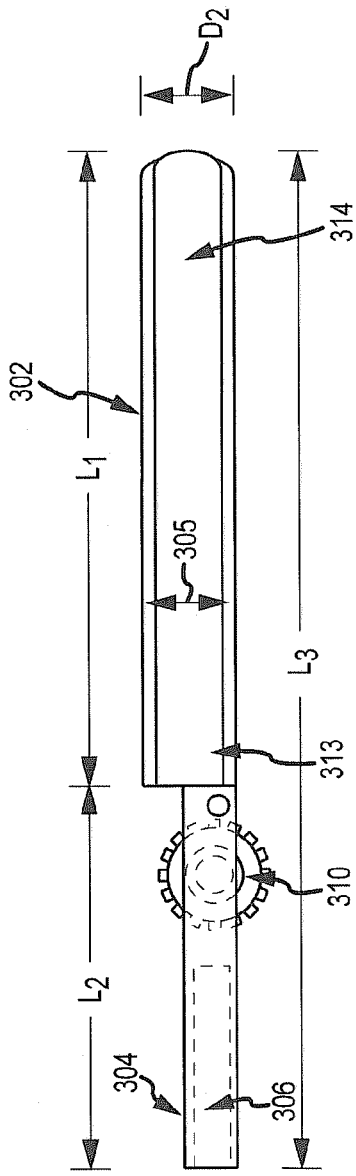
FIG. 3C is a side view of the speculum of FIGS. 3A-3B in the contracted configuration.
Figure 3D:
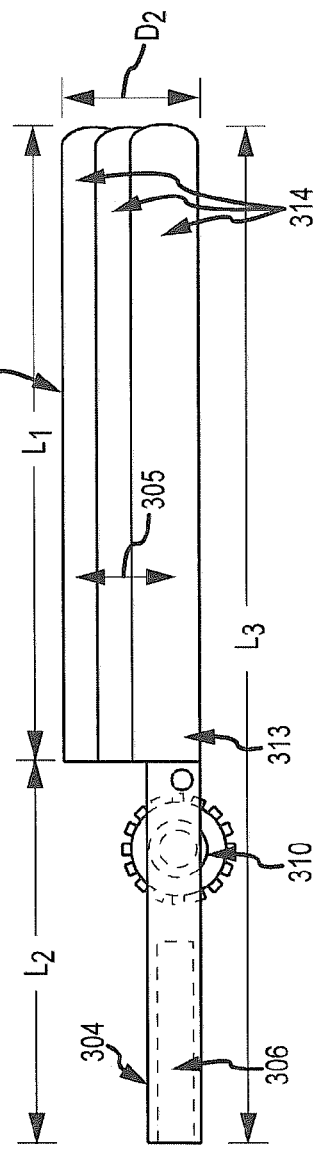
FIG. 3D is a side view of the speculum of FIG. 3A in the expanded configuration.
Figure 3E:
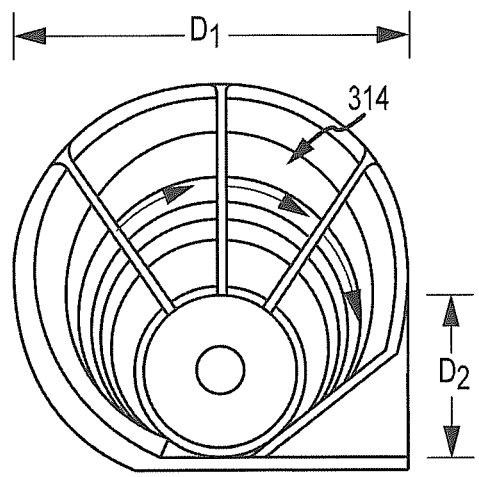
FIG. 3E is a end view of the dilation assembly of the speculum of FIGS. 3A-3B.

The speculum 300 of FIGS. 3A-3E shares many characteristics with the speculum of FIGS. 1A and 1B. For example, the speculum 300 is used by inserting the dilation assembly 302 into the patient's introitus with the speculum 300 in a contracted configuration (as shown in FIGS. 3B and 3C). The speculum 300 is then expanded to the expanded configuration (as shown in FIGS. 3A and 3D). The light source 308 can then be activated to illuminate patient's vaginal walls and cervix which can be inspected visually by looking through the hollow dilation assembly 302. Moreover, like the embodiment of FIGS. 1A and 1B, the speculum 300 expands radially with respect to multiple axes for improved viewing without interference due to collapsing vaginal walls.

However, the speculum 300 has some differences in relation to the embodiment of FIGS. 1A and 1B. In particular, where as the blades in FIGS. 1A and 1B are separated by spaces at least in the expanded configuration, the blades 314 of the speculum 300 overlap as can best be seen in FIGS. 3E and 3G. When the dilation assembly 302 is expanded or contracted, the blades slide circumferentially over one another (as generally indicated by arrows 305) in manner analogons to a collapsible colander. Accordingly, there are no spaces between the blades in either the expanded contracted configuration. This may further protect against collapsing of the vaginal walls and potential pinching.

Figure 3G:
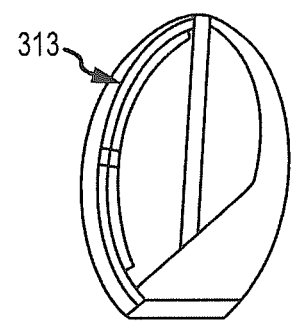
FIG. 3G is a expanded view of the linkage for interconnecting the worm gear racket assembly to the dilation assembly of the speculum of FIGS. 3A and 3B.
Figure 3F:
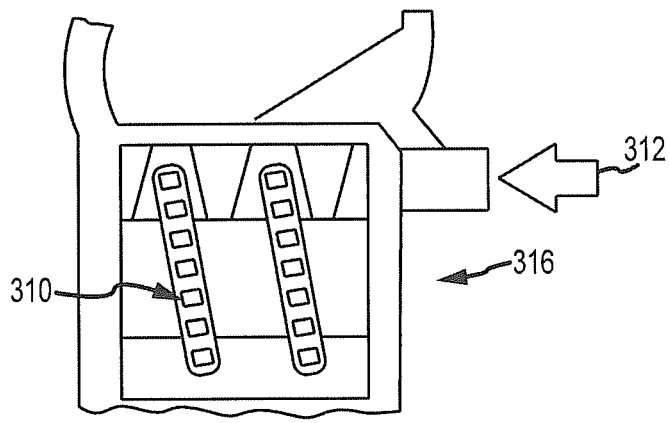
FIG. 3F is a expanded view of the worm gear ratchet mechanism of the speculum of FIGS. 3A and 3B.

Another difference between the illustrated speculum 300 and that of FIGS. 1A and 1B is the mechanism for actuating expansion of the dilation assembly 302. Specifically, the dilation assembly 302 is expanded by operation of the thumb lever 312. The thumb lever 312 interfaces with a worm gear ratchet as shown in FIG. 3F such that depressing the thumb lever closes the speculum 300 to the contracted configuration and pulling outwardly on the thumb lever 312 causes the speculum 300 to be expanded to the expanded configuration. The thumb lever 312 causes the worm gear of ratchet assembly 316 to rotate. The worm gear ratchet assembly 316 is then connected to the proximal ends 313 of the blades 314 by appropriate linkage (as shown in FIGS. 3F and 3G) to expand and contract the dilation assembly 302 as desired.

The illustrated speculum 300 is dimensioned to accommodate a range of patients including larger patients. For example, the diameter $D_1$, of the proximal end of the dilation assembly 302 may be about 1.5 inches. The diameter, $D_2$, of the distal end of the dilation assembly may be about 1.4 inches in the expanded configuration and about 0.7 inches in the contracted configuration. The dilation assembly 302 has a length, $L_1$, of about 6.5 inches and the handle 304 has a length, $L_2$, of about 3.5 inches for an overall length, $L_3$, of about 10 inches for the speculum 300.

FIGS. 4A-4E illustrate a still further embodiment of a speculum 400 in accordance with the present invention. The speculum 400 includes a number of overlapping speculum blades 402 generally similar to the blades in the embodiment of the FIGS. 3A-3G. In this case, however, the blades are expanded and contracted directly by rotating retention ring 404 rather than using a ratchet assembly as described in connection with the embodiment of FIGS. 3A-3G. In addition, the handle 406 is offset vertically from the expansion assembly 408 which may facilitate visual inspection through the expansion assembly 408. The handle 406 further includes a receptacle 410 for receiving a light source and a light pipe 412 for directing light from the source to the patient's cervix. FIGS. 5A-5F illustrate a speculum 500 in accordance with a still further embodiment of the present invention. The speculum 500 is similar to the speculum 100 of FIGS. 1A-1B, with some additional features shown and minor differences in configuration. The speculum 500 generally includes: a generally conical dilation assembly 502 including a number of blades 504; a generally cylindrical obturator 506 for expanding the dilation assembly 502 and allowing it to contract; and a handle 508 including a receptacle 510 for receiving a light source 512. As discussed above, the speculum can be formed, for example, from clear plastic or metal as desired.

The illustrated blades 504 are formed in an overlapping, collapsible configuration. That is, adjacent blades 504 extend circumferentially over one another, and slide over one another as the dilation assembly 502 is expanded and contracted. In this manner, gaps between the blades 504 are avoided, even in the expanded configuration, thus reducing the likelihood that tissue of the patient will be pinched due to operation of the speculum 500.

The speculum 500 further includes a ratchet mechanism 514 for advancing and withdrawing the obturator 506 into and out of the dilation assembly 502. The ratchet mechanism 514 includes a ratcheted handle surface 516 that interfaces with a bottom of a thumb lever 518. The thumb lever 518 includes an advance surface 520 and a release surface 522. The physician or other user can press on the advance surface 520, as generally indicated by arrow 524, to move the thumb lever 518 forward. The thumb lever 518 presses against the obturator 506 so that it also moves forward thus expanding the dilation assembly 502. The ratchet mechanism 514 is then effective to hold the speculum in the expanded configuration.

To release the ratchet mechanism 514 so that the obturator 506 can be withdrawn from the dilation assembly 502 to close the blades 504, the user can press on the release surface 522 as generally indicated by arrow 526. This causes the rear edge of the thumb lever 578 to lift and disengages the ratchet mechanism 514. The user can then slide the thumb lever 518 rearwardly to withdraw the obturator 506 from the dilation assembly 502.

As noted above, the handle 508 includes a receptacle 510 for receiving a light source 512. Although any appropriate light source can be used, the illustrated receptacle 510 can receive a low-cost pen light type of light source 512, thereby reducing costs and inconvenience in relation to some conventional systems. The light source 512 may have an on/off button at its rear end that can be easily accessed by the user during a procedure. Light from the light source is guided through the handle 508, and directed through the dilation assembly 502 to the procedure site by a plastic light pipe 528. Optionally, a brightly colored tag 530 or strap may be attached to the light source 512 to assist in locating the light source and to remind the user not to accidentally dispose of the light source 512 when the speculum 500 is discarded after a single use.

The blades 504 of the illustrated speculum 500 overlap, as indicated by arrow 532, so that there are substantially no spaces between the blades 504 in the expanded configuration. In this regard, the blades 504 may move linearly (or arcuately with substantially no circumferential component) in a radial direction when expanding while maintaining their overlapped, stacked relationship at their proximal ends like flower petals, or the blades 504 may slide circumferentially over one another while expanding like an expandable colander.

Figure 5C:
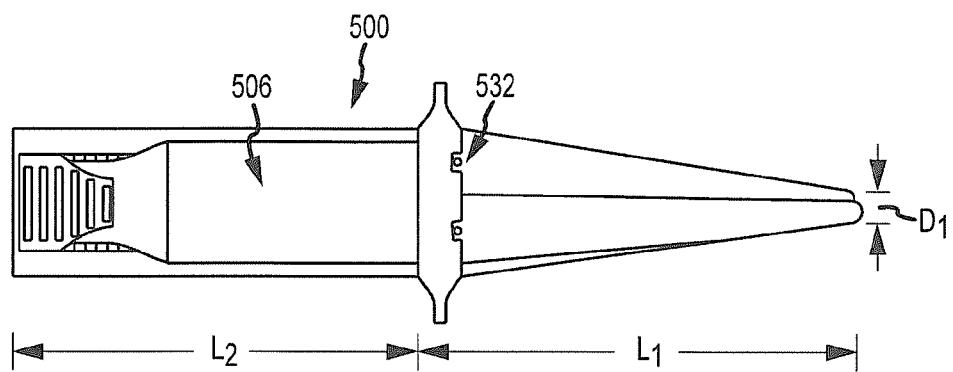
FIGS. 5C-5D, are top views of the speculum of FIGS. 5A-5B in the closed and open configurations, respectively.
Figure 5D:
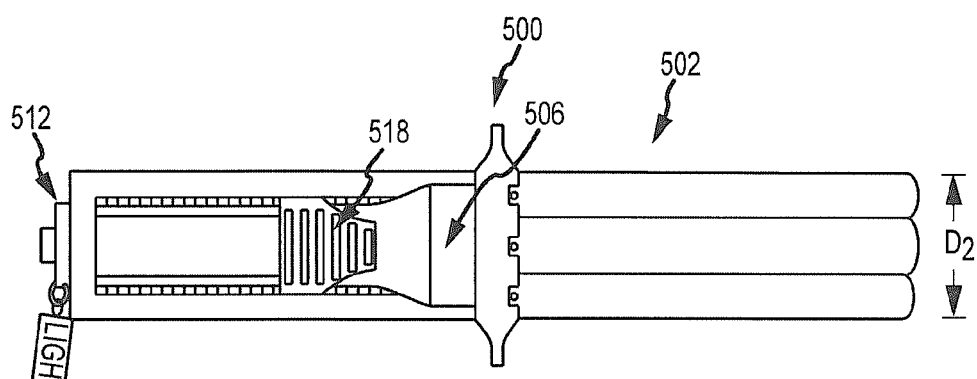
Figure 5E:
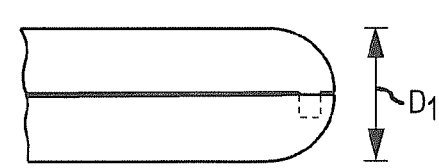
FIGS. 5E-5F are side views of distal end blade portions of the speculum of FIGS. 5A-5B in the closed and open configurations, respectively.
Figure 5F:
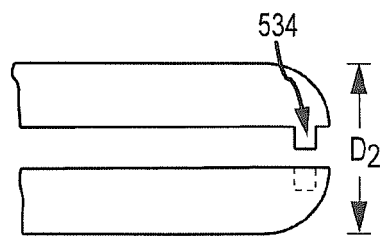

The speculum 500 is preferably dimensioned to accommodate a range of patients. For example, the dilation assembly 502 may have a length $L_1$, of about 3.5 inches and the handle 508 may have a length, $L_2$, of about 3.5 inches for an overall speculum length of 7 inches. In the contracted configuration, the distal end of the dilation assembly 502 has a diameter, $D_1$, of about 1.5 inches. The distal end of the dilation assembly 502 preferably has a bullet-shaped configuration, as can be seen in FIG. 5E, that helps maintain the assembly 502 in the contracted configuration as the assembly 502 is introduced into the introitus. Optionally, one or more pegs 534 and mating receptacles may be provided at the distal end of the dilation assembly 502 to further assist in maintaining the contracted configuration.

In the various embodiments disclosed above, the handles generally extend rearwardly in alignment with or at an acute angle to the longitudinal axis of the dilation assembly in each case.

What is claimed:
1. A vaginal speculum, comprising:
a handle adapted for gripping by a user;
a dilation assembly, connected to the handle, for separating and retaining vaginal walls of a patient so as to permit inspection of a cervix of the patient, said dilation assembly having a proximal end portion proximate to the handle and a distal end portion remote from the handle;
a dilation actuator, operatively associated with the dilation assembly, for moving the dilation assembly between a contracted configuration, wherein the distal end portion has a reduced circumference to facilitate introduction of the dilation assembly with the patient and withdrawal therefrom, and an expended configuration, wherein the distal end portion is expanded to define an enlarged visualization aperture; and said dilation actuator being operative to expand said distal end portion of said dilation assembly in relation to at least a first axis and a second axis transverse to said first axis.

2. A speculum as set forth in claim 1, wherein said dilation assembly includes at least first and second blades extending from said proximal end portion to said distal end portion, each of said blades being moveable in relation to a central axis of said dilation assembly that is stationary with respect to said handle.

3. A speculum as set forth in claim 1, wherein said dilation assembly comprises first, second and third blades extending from said proximal end portion to said distal end portion.

4. A speculum as set forth in claim 3, wherein said second blade is movable with respect to said first blade and said third blade is movable with respect to each of said first blade and said second blade.

5. A speculum as set forth in claim 3, wherein said dilation assembly has a generally conical shape in said contracted configuration, substantially centered in relation to an axis that is fixed.

6. A speculum as set forth in claim 1, wherein said dilation assembly has a generally conical shape, in said contracted configuration, wherein said dilation assembly is wider at said proximal end portion than at said distal end portion, and said dilation actuator comprises an obturator adapted to be inserted into a hollow interior of said dilation assembly at said proximal end portion and withdrawn therefrom so as to move said dilation assembly between said contracted and expanded configurations.

7. A speculum as set forth in claim 6, wherein said obturator comprises a generally cylindrical tube.

8. A speculum as set forth in claim 7, wherein said obturator is operative to be substantially linearly advanced into and out of said dilation assembly.

9. A speculum as set forth in claim 7, wherein said obturator is advanced into and withdrawn from said dilation assembly by a screw mechanism.

10. A speculum as set forth in claim 1, wherein said dilation assembly is centered about an axis extending from said proximal end portion to said distal end portion, and said handle is disposed at an angle of no more the 45° with respect to said axis.

11. A speculum as set forth in claim 1, further comprising a light source receptacle assembly for receiving a light source such that light can be directed through said dilation assembly to a procedure site.

12. A method for use in performing a medical procedure on a patient, comprising the steps of:
providing a speculum including a dilation assembly and a dilation actuator;
introducing the dilation assembly into the introitus of a patient;
after said step of introducing, first operating said dilation actuator to expand the dilation assembly with respect to a first axis and with respect to a second axis transverse to said first axis; and
upon concluding a medical procedure, second operating said dilation actuator to contract said dilation assembly to a contracted configuration and withdrawing the dilation assembly from the introitus of the patient.

13. A method as set forth in claim 12, wherein said dilation assembly includes at least three blades disposed about a central longitudinal axis, and said step of first operating comprises moving each of said three blades outwardly away from said central, longitudinal axis.

14. A method as set forth in claim 12, wherein said step of first operating comprises advancing an abturator into a hollow interior of the dilation assembly.

* * * * *